US007851643B2

(12) United States Patent
Hillion et al.

(10) Patent No.: US 7,851,643 B2
(45) Date of Patent: Dec. 14, 2010

(54) METHOD OF MANUFACTURING FATTY ACID ETHYL ESTERS FROM TRIGLYCERIDES AND ALCOHOLS

(75) Inventors: Gérard Hillion, Herblay (FR); Bruno Delfort, Paris (FR)

(73) Assignee: IFP Energies Nouvelles, Rueil Malmaison Cedex (FR)

( * ) Notice: Subject to any disclaimer, the term of this patent is extended or adjusted under 35 U.S.C. 154(b) by 1125 days.

(21) Appl. No.: 11/521,613

(22) Filed: Sep. 15, 2006

(65) Prior Publication Data

US 2007/0066838 A1 Mar. 22, 2007

(30) Foreign Application Priority Data

Sep. 16, 2005 (FR) .................... 05 09526

(51) Int. Cl.
*C11C 3/00* (2006.01)
*C10L 1/18* (2006.01)

(52) U.S. Cl. .................. 554/167; 554/168; 554/170; 554/174; 44/308

(58) Field of Classification Search .............. 554/174, 554/178
See application file for complete search history.

(56) References Cited

U.S. PATENT DOCUMENTS

| 5,885,946 A | 3/1999 | Lamsa |
| 5,908,946 A | 6/1999 | Stern et al. |
| 7,420,073 B2 * | 9/2008 | Hillion et al. ............... 554/174 |
| 7,605,281 B2 * | 10/2009 | Oku et al. .................... 554/170 |
| 2005/0113588 A1* | 5/2005 | Hillion et al. ............... 554/174 |

FOREIGN PATENT DOCUMENTS

| FR | 2752242 A | 2/1998 |
| FR | 2866654 A | 8/2005 |
| WO | WO2005/021697 | * 3/2005 |

* cited by examiner

*Primary Examiner*—Jafar Parsa
*Assistant Examiner*—Yate' K Cutliff
(74) *Attorney, Agent, or Firm*—Millen, White, Zelano & Branigan, P.C.

(57) ABSTRACT

A method of manufacturing an ester composition comprising ethyl esters of linear monocarboxylic acids having 6 to 26 carbon atoms from a vegetable or an animal oil, neutral or acid, virgin or recycled, the method comprising: a stage 1 of reaction of vegetable or animal oil with methanol, in the presence of a heterogeneous catalyst comprising a combination of at least one metallic oxide and alumina or a combination of at least two metallic oxides and possibly alumina, and a stage 2 of reaction of the product from stage 1 with ethanol in the presence of a heterogeneous catalyst as defined for stage 1, so as to obtain from vegetable or animal oils, a mixture of fatty acid esters rich in fatty acid ethyl esters and a glycerin of high purity.

12 Claims, 2 Drawing Sheets

METHOD OF MANUFACTURING FATTY ACID ETHYL ESTERS FROM TRIGLYCERIDES AND ALCOHOLS

FIELD OF THE INVENTION

The present invention relates to the manufacture of monocarboxylic acid ethyl esters from vegetable or animal oils.

It more particularly relates to a new method of producing ethyl esters of linear monocarboxylic acids having 6 to 26 carbon atoms by means of a succession of two stages.

BACKGROUND OF THE INVENTION

Esters of fatty substances are currently used in many applications as diesel fuel, heating oil, ecological solvents, base compounds for the manufacture of fatty acid sulfonates, amides, ester dimers, etc.

In the case of diesel fuel, which is today a major application of fatty substance esters, a certain number of specifications were established whose list, limits and methods belong to the EN 14214 (2003) standard currently applicable in Europe. The ester must contain at least 96.5% by mass of esters, at most 0.8% by mass of monoglycerides, at most 0.2% by mass of diglycerides and at most 0.2% by mass of triglycerides, few free fatty acids, that may be corrosive, less than 0.25% by mass of bound and free glycerin and no strong acids or metal traces at all. This requires a precise protocol to obtain the desired purity.

In the case of heating oil, it is obvious that all these specifications are not always useful and even sometimes detrimental but, the heating oil market and the gas oil market being often confused, the heating oil specifications resemble the gas oil specifications because, in France, heating oil can be used in agricultural tractors and building engines.

When manufacturing an ester from oil or grease and monoalcohol, 10 to 15% by mass of a by-product which is glycerin automatically forms, depending on the nature of the oil initially used. This glycerin is sold at a high price for various uses, but only when it is of high purity, which is obtained after intensive purification operations in specialized vacuum distillation plants.

In short, most commercial ester manufacturing methods quite readily lead to raw products (esters and glycerin) that however have to be purified in depth by means of various treatments that eventually put a strain on the transformation cost.

Thus, during the manufacture of methyl esters of fatty substances from refined oils and dry alcohol, whereas simple alkaline derivatives such as sodium alcoholates, soda or potash are commonly used as catalysts under rather mild conditions (temperature from 50° C. to 80° C. and atmospheric pressure), as can be read in many patents or publications, for example in the JAOCS 61, 343-348 (1984), a pure product that can be used as fuel and a glycerin meeting the specifications can however be obtained only after a great many stages.

If we take for example the most commonly used alkaline catalysts, we find, in the glycerin as well as in the ester, traces of alkaline compounds that have to be removed by washing and drying the ester fraction. In the glycerin phase, the soaps and alcoholates present have to be neutralized, the salts formed have to be filtered, the glycerin has to be evaporated after removing the water, unless the diluted glycerin is passed on ion-exchanging resins, prior to concentrating the salt-free glycerin. Finally, the excess alcohol always has to be evaporated and often distilled, while preventing this evaporation, especially when it is carried out in the ester phase, from causing the ester present to react with the partly dissolved glycerin, which would lead to the formation of monoglycerides.

In short, to obtain the wanted specifications for the glycerin and the ester, so many stages have to be performed that only large plants can be economically profitable under such conditions.

Furthermore, although vegetable or animal oil esters for use as diesel fuel are most often methyl esters, it is also possible to use vegetable or animal oil ethyl esters. The latter are prepared from ethanol instead of methanol, which leads, when the ethanol is of renewable origin, to a biodiesel fuel whose origin is 100% renewable, which is not the case with fatty acid methyl esters, methanol being generally obtained from fossil material.

Manufacture of fatty acid ethyl esters can also be preferred in geographical zones where ethanol is more plentiful or more readily available than methanol.

SUMMARY OF THE INVENTION

Surprisingly, it has been discovered that it is possible to economically obtain, from vegetable or animal oils, a mixture of fatty acid esters rich in fatty acid ethyl esters and a glycerin of high purity by means of two stages using methanol during the first stage and ethanol in the second.

DETAILED DESCRIPTION

Figure 1:
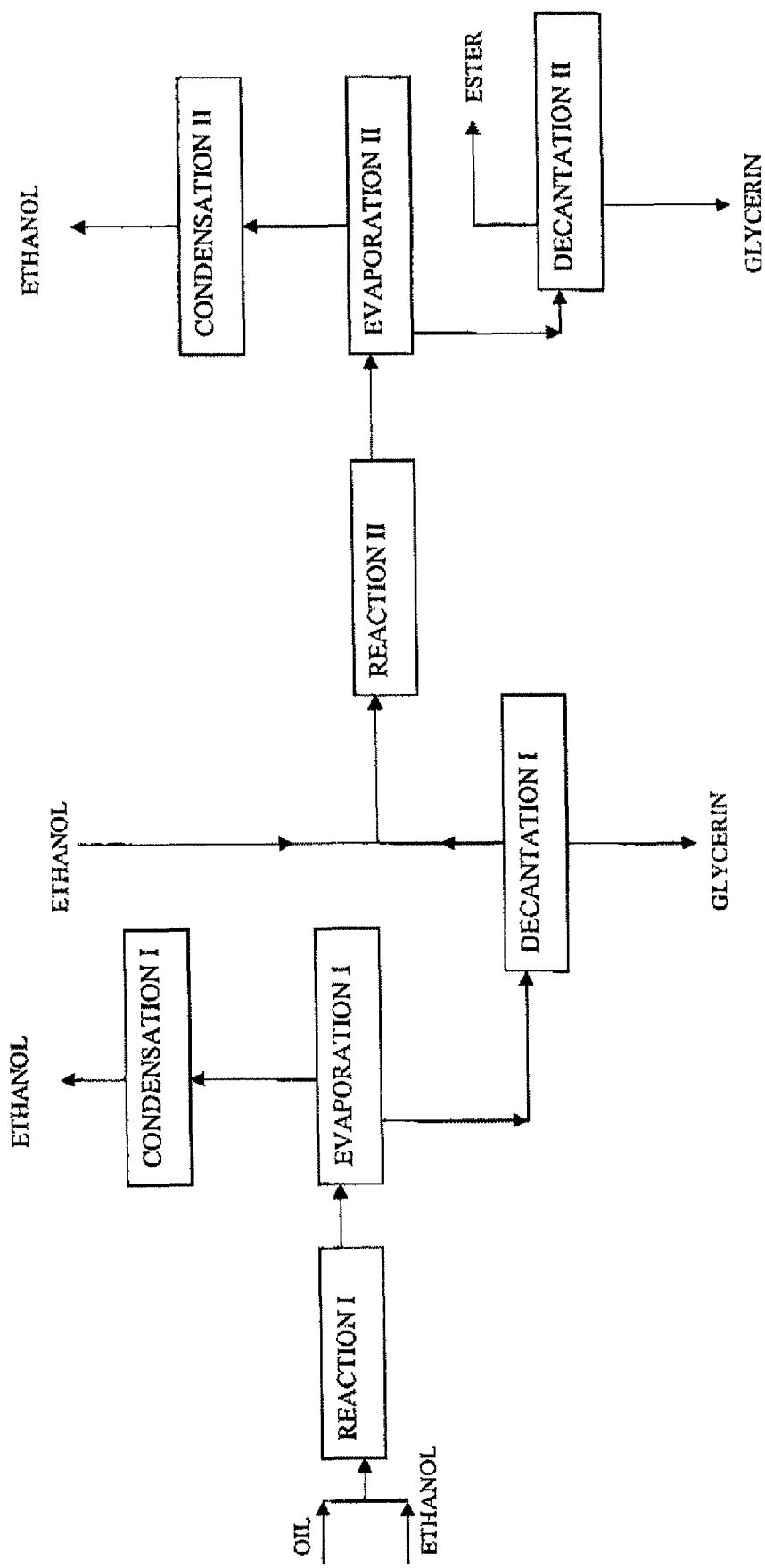
FIG. 1 shows the flowsheet of a heterogeneous process using two transesterification stages wherein the alcohol involved is ethanol.

The invention thus provides a method of manufacturing ethyl esters of linear monocarboxylic acids having 6 to 26 carbon atoms, by reaction of vegetable or animal oils, neutral or acid, virgin or recycled, in the presence of a heterogeneous catalyst comprising a combination of at least one metallic oxide and alumina or a combination of at least two metallic oxides and possibly alumina, said method being characterized in that it combines two successive transesterification stages, the first one using methanol and the second ethanol.

The two stages of the method according to the invention are more particularly described hereafter:

Stage 1

It comprises the reaction of at least one vegetable or animal oil, neutral or acid, virgin or recycled, with methanol, in the presence of a heterogeneous catalyst comprising a combination of at least one metallic oxide and alumina or a combination of at least two metallic oxides and possibly alumina.

The reaction that is mainly aimed at in this stage is transesterification carried out according to Scheme I hereafter, illustrated here with oleic fatty chains.

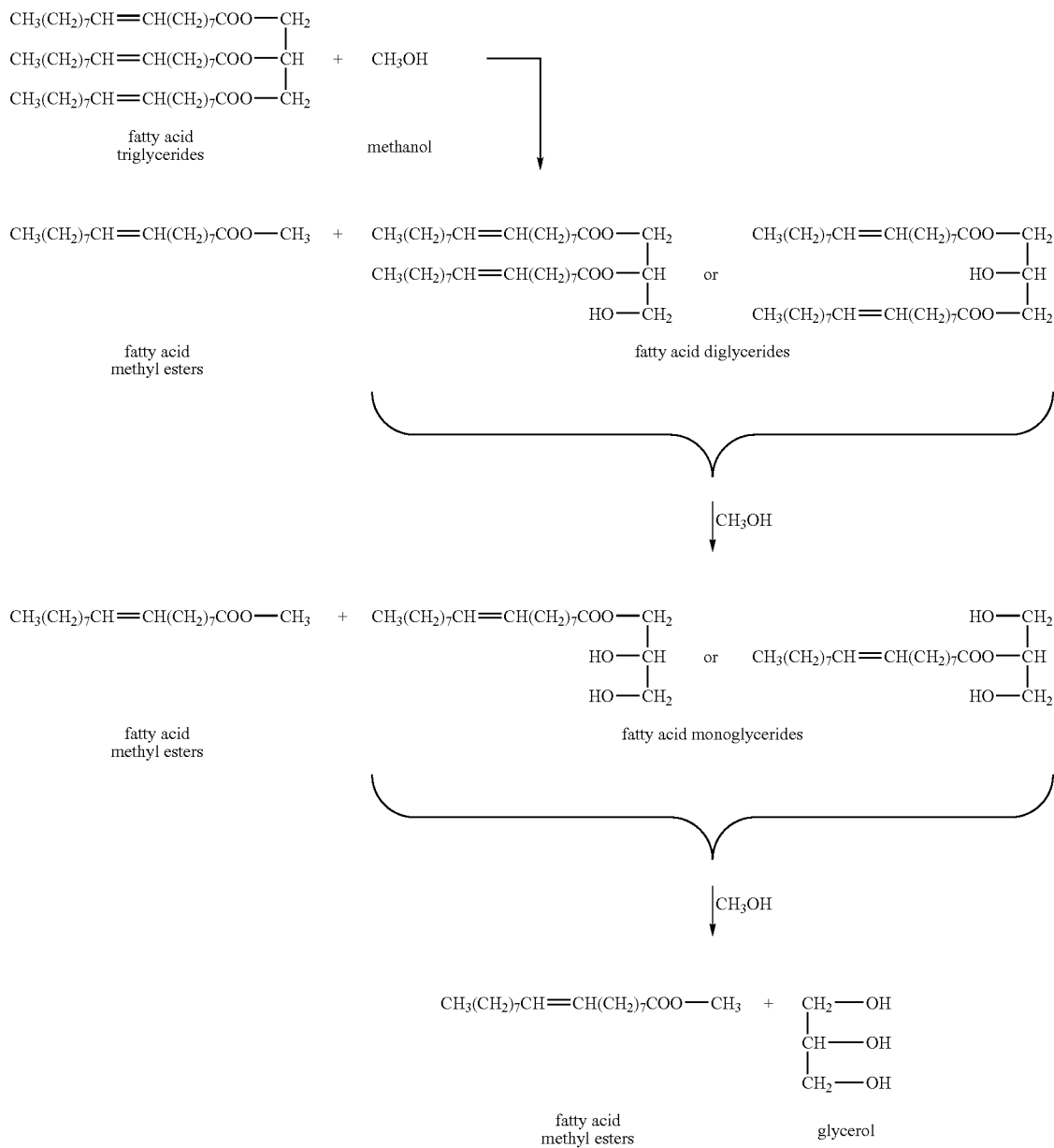

Scheme I

The product obtained predominantly contains fatty acid methyl esters, but it also contains fatty acid monoglycerides and diglycerides, which are intermediate conversion products, as well as residual fatty acid triglycerides.

Stage 2

It comprises the reaction of the product from stage 1 with ethanol in the presence of a heterogeneous catalyst defined in the same manner as the heterogeneous catalyst used in stage 1.

The conversion carried out in this stage leads to fatty acid ethyl ester and methyl ester compositions, rich in ethyl esters, whose monoglyceride, fatty acid diglyceride and residual fatty acid triglyceride concentrations are compatible with the specifications required for the products to be usable as fuel or cofuel for diesel engines.

The reactions that are mainly aimed at in stage 2 are trans-esterifications carried out according to Scheme II hereafter, illustrated here with oleic fatty chains.

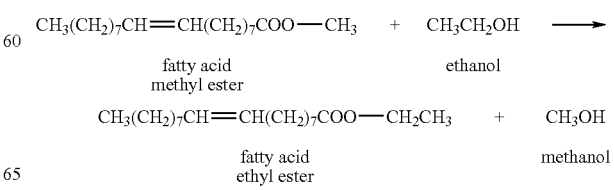

Scheme II but also according to the following scheme:

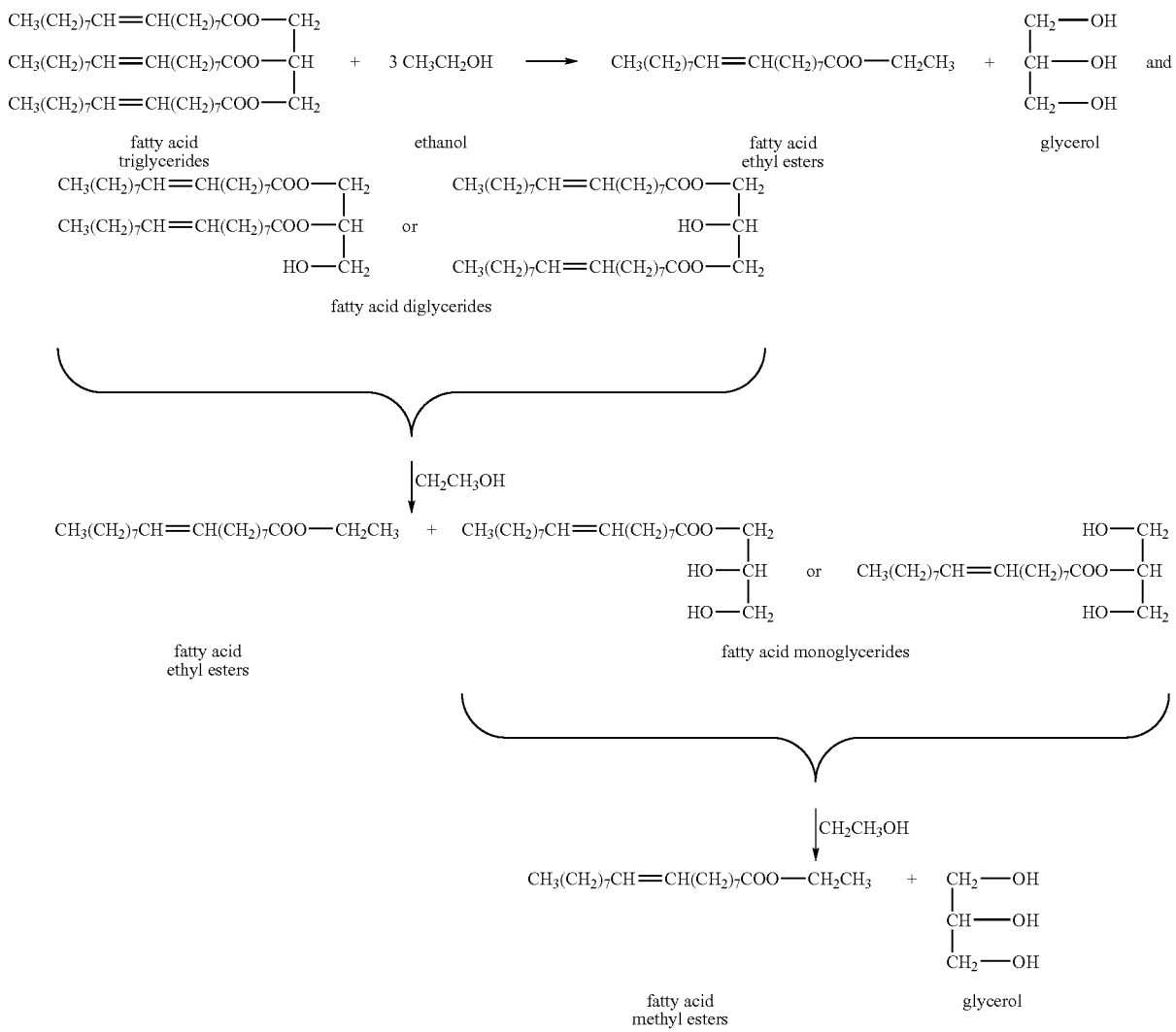

In the two transesterification stages of the method according to the invention, what is understood to be a heterogeneous catalyst is any solid catalyst allowing transesterification of a mixture of triglycerides such as a natural fatty substance (oil or grease) to a mixture of alkyl esters. The heterogeneous catalyst can be selected more particularly from the metallic oxides and the oxide mixtures likely to form with one another, and possibly with alumina, oxide combinations.

The use of heterogeneous catalysts is not new. However, it appears that no industrial process allows to economically obtain both an ester and a glycerin of high purity. To produce economically means to obtain an ester meeting the standards and a pure glycerin, at a good space velocity or within reasonable time limits and without sustained scrubbing.

An example of a document from the prior art dealing with heterogeneous catalysts is European patent EP-B-0,198,243. The transesterification catalyst that converts oil and methanol to methyl ester is an alumina or a mixture of alumina and of ferrous oxide. In the examples, the column used for the fixed bed has a volume of 10 liters and oil is generally injected at a rate below 1 liter/hour, which gives a LHSV (LHSV=volume of oil injected/volume of catalyst/hour) below 0.1. For a 100 000 t/year plant, this would correspond to reactors of at least 150 m$^3$. Another problem that seems to arise is the amount of glycerin collected, which is much less than the amount expected in theory. In no example where 10% by mass of glycerin is to be collected is this value obtained, even approximately. Finally, the purity of the esters is rather low, from 93.5 to 98%. What becomes of the glycerin that has not been collected is not mentioned. In some cases, glycerin esters form, as mentioned in this patent; in other cases, maybe it decomposes, unless it is eliminated in a first stage. The performance level is thus rather low. It can be noted that, at the LHSVs mentioned and for contact times above 6 hours, 80% and even higher conversion rates can be obtained even without a catalyst.

This patent therefore does not seem to provide a reasonable solution from an economical point of view.

British patent application GB-A-795,573 describes the use, as the catalyst, of a zinc silicate at temperatures ranging between 250° C. and 280° C. and at a pressure of at least 100 bar (10 MPa) with methanol. A 85% conversion seems to be obtained in a first stage, and even 100% if the glycerin is allowed to settle in an intermediate stage and the reaction is continued. According to patent EP-B-0,198,243, which mentions GB-A-795,573, zinc soaps that of course have to be banned from fuels formed with the zinc compounds. This seems to be due to the high temperatures that are required in this reaction with this catalyst.

Since then, a new generation of heterogeneous catalysts allows to obtain, from vegetable or animal oils and monoalcohols, esters of high purity meeting the specifications of the EN 14214 standard, and a colourless and sometimes odourless glycerin, depending on the post-treatment applied, decolorizing with coal, activated clay, other adsorbents, etc. The methods used with these heterogeneous catalysts are performed either continuously, in a fixed bed for example, or discontinuously. The catalysts consist of a catalytic system based on metallic oxides, alone or combined, deposited on an alumina or not.

Patents filed by the applicant that use catalysts based on metallic oxides and alumina can be mentioned: notably patent FR-B-2,752,242, which describes the use of solid and non-soluble catalysts formed from zinc oxide and alumina or zinc aluminate, French patent FR-B-2,838,433, and the published French patents FR-A-2,855,517; 2,855,518; 2,855,519; 2,869,612 and 2,869,613.

All these catalysts come in form of powder, balls, extrudates or pellets. However, the combination of alumina in catalytic systems has two favourable effects. The first one is to often increase the surface area, the second to create a much more stable compound, notably under conditions where the metal making up the oxide would tend to form metallic soaps.

Another interest of oxide-based catalysts is their capacity to catalyse the transesterification of oil with alcohols heavier than methanol. Thus, it is possible to form ethyl, isopropyl or butyl esters which are of interest in fuels because the pour points of esters formed with these alcohols are often lower than those of methyl esters, the gain sometimes reaching 10° C., which allows more saturated oils to be used initially.

Examples of metallic oxides that can be used in the oxide combinations are, apart from alumina, oxides of the metals from group IIA such as magnesium, calcium, strontium and barium, from group IIB such as zinc and cadmium, from group IIIA such as gallium and indium, from group IIIB such as scandium, yttrium, lanthanum, actinium, cerium and thorium, from group IVB such as titanium, zirconium and hafnium, from group IIIA such as gallium, indium and thallium, from group IVA such as germanium, tin and lead, and from group VA such as arsenic, antimony and bismuth.

Their general formulas, for a combination of a single oxide with alumina, is as follows: $(M^1O_x)_y(Al_2O_3)_{(1-y)}$, (x having a value from 1.2 to 2.6 and y being the mass ratio of the two oxides having a value from 0.005 to 2).

For a combination of two metal oxides $M^1$ and $M^2$, possibly in the presence of alumina, we have the general formula:

$$[M^1_a M^2_b O_c]_y [(Al_2O_3)]_{(1-y)}$$

(where a has a value from 0.5 to 5, b a value from 0.5 to 5, c is the number of oxygen atoms that satisfies the valence of metals $M^1$ and $M^2$ and y has a value from 0.005 to 1).

The two stages of the method according to the invention are carried out under conventional operating conditions, for example at a temperature from 165° C. to 240° C., with a contact time from 15 minutes to 3 hours and an alcohol/feedstock mass ratio from 20/80 to 80/20.

It has been observed that the sequence of these two stages, the first one with methanol and the second with ethanol, according to the method of the invention, affords certain advantages in relation to a conventional heterogeneous method (as described for example in patent U.S. Pat. No. 5,908,946 filed by the applicant, or FR-B-2,752,242 mentioned above) wherein the two stages are carried out with ethanol to obtain fatty acid ethyl esters.

Examples of oils that can be used in the method according to the invention are all the common oils, such as palm oil (concrete or olein), soybean oil, palm nut oil, copra oil, babassu oil, colza oil (old or new), sunflower oil (conventional or oleic), corn oil, cotton oil, tallow and lard, peanut oil, pourgher oil (*Jatropha curcas*), castor oil, lineseed oil and crambe oil, and all the oils obtained from sunflower and colza for example by genetic engineering or hybridization.

It is even possible to use waste kitchen oil, slaughterhouse oil, various animal oils such as fish oil, seal oil, and even fowl fat, because the esters manufactured from certain alcohols allow to gain more than 10° C. in pour point.

The oils used can also include partly modified oils, for example by polymerization or oligomerization.

The presence of fatty acids in the oils is not harmful in principle because oxide-based catalytic systems are also active for esterification and they also convert fatty acids to esters. The limit value for the free fatty acids contained in oils ranges around an acid number close to 10. The operability of the method under such conditions is close to that defined with an oil having a low acid number.

In the case of oils with a very high acid number, one option consists in preceding the transesterification reaction by an esterification reaction of the free fatty acids present, using either the same alcohol as the alcohol used in the transesterification method in the presence of a strong acid such as sulfuric acid or soluble or supported sulfonic acids (of Amberlyst 15® resins type) or preferably glycerin, to form a total or partial glycerol ester, using the same type of catalyst based on metallic oxides, at atmospheric pressure and preferably under partial vacuum, and at temperatures ranging between 180° C. and 240° C.

With waste kitchen oils, which are a very cheap raw product for the production of a biodiesel fuel, the fatty acid polymers will have to be removed from the reaction mixture so that the mixture of esters meets the specifications of the EN 14214 standard.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

EXAMPLES

The following examples illustrate the invention, examples 1, 3 and 5 being given by way of comparison.

The oil used in these examples is colza oil whose fatty acid composition is as follows:

| Fatty acid glyceride | Nature of the fatty chain | % by mass |
|---|---|---|
| Palmitic | C16:0 | 5 |
| Palmitoleic | C16:1 | <0.5 |
| Stearic | C18:0 | 2 |

-continued

| Fatty acid glyceride | Nature of the fatty chain | % by mass |
|---|---|---|
| Oleic | C18:1 | 59 |
| Linoleic | C18:2 | 21 |
| Linolenic | C18:3 | 9 |
| Arachidonic | C20:0 | <0.5 |
| Gadoleic | C20:1 | 1 |
| Behenic | C22:0 | <0.5 |
| Erucic | C22:1 | <1 |

However, any other oil of vegetable or animal origin could give similar results.

Example 1

Comparative

Example 1 details the operating conditions of a heterogeneous process using two transesterification stages wherein the alcohol involved is ethanol. These two stages are necessary to reach the purity level required from a mixture of esters intended for use as a fuel, according to the EN 14214 standard. The flowsheet is given in FIG. 1.

Description of the Experimental Setup

The experiment is carried out in a device comprising a fixed bed reactor, i.e. a filled column, 1.9 cm in diameter and 120 cm in length, heated by three shells surrounding the column. Preheating of the oil and of the alcohol is performed in the column on 10 cm³ glass balls and the reaction occurs on 110 cm³ of a solid catalyst essentially consisting of zinc aluminate in form of approximately 2 mm-diameter extrudates, meeting the formula: $ZnAl_2O_4$, x ZnO, y $Al_2O_3$ (x and y ranging each between 0 and 2) and prepared according to a protocol described in patent FR-B-2,752,242. At the column outlet, 20 cm³ tungsten carbide and 5 cm³ glass balls are added. The inverted U-shaped device consists of a tubular reactor, a cooling element on the horizontal part and a settler that makes up the second branch. In the upper part of the settler, a gas purge system allows to control the pressure, i.e. to maintain it first with nitrogen at the desired pressure from 15 to 60 bar (1-6 MPa). The settler is provided with a liquid purge at the lower outlet thereof. When the settler is half full, an automatic valve opens so as to partly drain the product obtained. Two pumps inject at the selected flow rates and at a constant pressure the alcohol and the oil into the column, from the bottom up.

After collecting the product made up of alcohol, glycerol and ester, generally present in a single phase, the alcohol is evaporated, then the ester and the glycerol are separated by decantation. Analysis of the ester phase is carried out by steric exclusion chromatography. The composition of the mixture is expressed in % by weight. The LHSV is the volume of oil injected per volume of catalyst and per hour. The residence time takes account of the presence of alcohol; it is determined by the relation:

$$\frac{120 \text{ cm}^3 \text{ catalyst} \times 60(*)}{\text{volume of oil in cm}^3 + \text{volume of alcohol in cm}^3 \text{ (injected in 1 hour)}}$$

(*) time expressed in minutes.

Experimentation

Example 1

100 g colza oil and 100 g ethanol are fed at 200° C. and at a LHSV of 0.25 h⁻¹ (volume of oil per volume of catalyst and per hour) into a fixed-bed reactor containing 110 ml of a catalyst consisting of a mixed zinc aluminate oxide.

After a residence time of about 110 minutes, a mixture consisting of about 93.2% by mass of ethyl esters, 3.7% by mass of monoglycerides, the 100% complement being made up of triglycerides, diglycerides, sterols and sterol esters, is obtained. This composition is not compatible with the specifications required by the EN 14214 standard for use of this product as a fuel, at least as regards the proportions of esters and of monoglycerides. The reaction therefore has to be continued to improve the conversion.

To carry out a second catalysis stage, it is necessary to remove all or part of the glycerin formed during the first stage in order to shift the reaction equilibrium. An excess ethanol flash is readily obtained by expansion by going from 200° C. to 90° C., where at least 75% of the ethanol present is removed. Under such conditions, a large part of the glycerin is removed by decantation. The ester phase is then fed with an ethanol complement into a second reactor similar to the first one to be subjected to a complementary conversion stage.

During this second stage, the temperature, the residence time and the amount of ethanol are adjusted so as to meet the specifications required for the product to be able to be used as biodiesel fuel according to the EN 14214 standard: at least 96.5% by mass of esters, at most 0.8% by mass of monoglycerides, at most 0.2% by mass of diglycerides and at most 0.2% by mass of triglycerides. For an ethanol/ester phase mass ratio of 1/1, at 200° C., the required reaction time to reach the conversion allowing the specifications to be met for biodiesel fuel is 110 minutes.

At this stage, the excess ethanol contained in the ester mixture thus obtained has to be again removed by evaporation. A second glycerin fraction representing about 10 to 12% of the total glycerin formed during the transesterification reaction can then be removed by decantation. The residual ethanol is then totally removed by distillation, which is the last stage of purification of the ester fraction. The biodiesel fuel yield is close to the theoretical maximum value because, in this case, the unsaponifiable compounds naturally present in the oil are contained in the biodiesel fuel.

Example 2

According to the Invention

Figure 2:
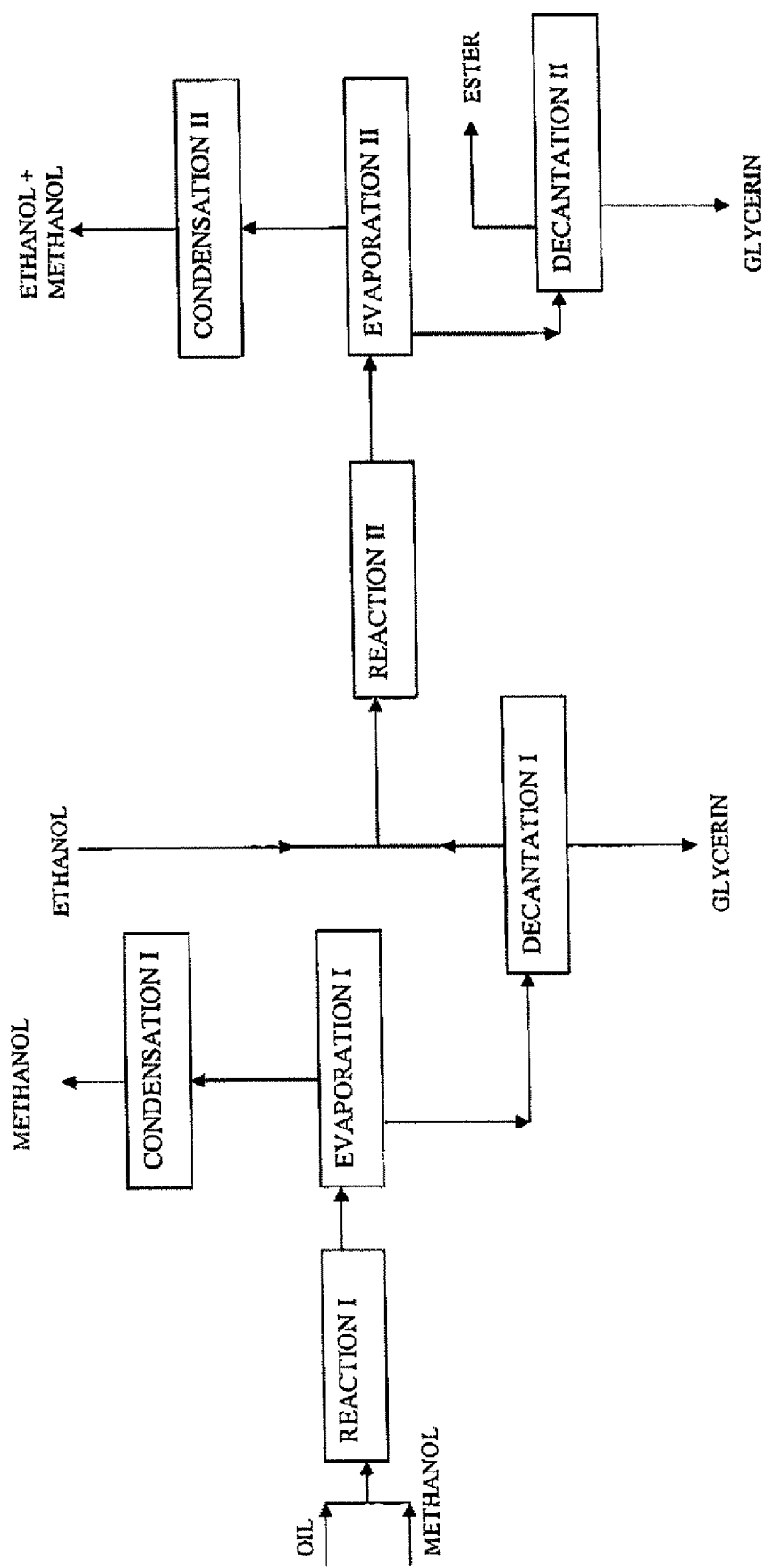
FIG. 2 shows the flowsheet of a heterogeneous process involving a first transesterification stage wherein the alcohol used is methanol and a second stage wherein the alcohol used is ethanol.

This example describes the operating conditions of the method involving a first transesterification stage wherein the alcohol used is methanol and a second stage wherein the alcohol used is ethanol. The flowsheet is given in FIG. 2.

As in example 1, 100 g colza oil and this time 100 g methanol are fed into a fixed-bed reactor containing 110 ml of the same catalyst, at 200° C., at a LHSV of 0.5 h⁻¹ (volume of oil per volume of catalyst and per hour), i.e. a reaction time of 55 minutes. The composition of the reaction mixture at the end of this reaction time is of the order of 93.9% by mass of methyl esters and 3.4% by mass of monoglycerides, the 100% complement consisting of residual triglycerides, diglycerides, sterols and sterol esters.

The next stage consists in removing all of the excess methanol, in decanting the glycerin formed, then in continuing the operation by means of a second reaction stage wherein the ester phase is fed with ethanol into a second reactor similar to the first one in order to be subjected to a conversion to fatty acid ethyl esters.

During this second reaction stage, the temperature, the residence time and the amount of ethanol are adjusted so as to meet the specifications required for the product to be able to be used as biodiesel fuel: at least 96.5% by mass of esters, at most 0.8% by mass of monoglycerides, at most 0.2% by mass of diglycerides and at most 0.2% by mass of triglycerides. For an ethanol/ester phase mass ratio of 1/1, at 200° C., the required reaction time to reach the conversion allowing the specifications to be met for biodiesel fuel is 55 minutes.

The residual alcohol contained in the ester mixture thus obtained has to be again removed by evaporation. It is a mixture of ethanol and of ethanol-rich methanol. The two alcohols are separated by distillation according to procedures known to the man skilled in the art, then recycled to the process. A second glycerin fraction representing about 10 to 12% of the total glycerin formed during the transesterification reaction can then be removed by decantation. The biodiesel fuel yield is close to the theoretical maximum value because, in this case, the unsaponifiable compounds naturally present in the oil are contained in the biodiesel fuel.

The biodiesel fuel obtained consists of 97.5% of a mixture of fatty acid ethyl esters and of fatty acid methyl esters with an ethyl ester/methyl ester mass proportion of 72/28.

Thus, the procedure described above allows to prepare a biofuel consisting of fatty acid ethyl esters and fatty acid methyl esters rich in fatty acid ethyl esters, with reaction times in each one of the two stages of 55 minutes, instead of 110 minutes when the two stages are carried out each in the presence of ethanol, as described in example 1.

Example 3

Comparative 25 g colza oil, 25 g ethanol and 1 g of the catalyst described in example 1 are fed into a 100-ml autoclave reactor equipped with a stirring system and with a temperature and pressure control device. The medium is brought to 200° C. under stirring. The pressure reaches 32 bar (3.2 MPa).

A sample is taken from the liquid phase after a 7-hour reaction. After ethanol filtration and evaporation, the medium is allowed to settle. No phase separation is observed, which indicates a negligible free glycerol formation. The ethyl ester concentration is determined by steric exclusion chromatography. It is 23.8% by mass.

At this stage, 20 g of the product obtained above, 20 g ethanol and 1 g of the catalyst described in example 1 are fed into a 100-ml autoclave reactor equipped with a stirring system and with a temperature and pressure control device. The medium is brought to 200° C. under stirring. The pressure reaches 32 bar (3.2 MPa).

A sample is taken from the liquid phase after a 7-hour reaction. After filtration and evaporation of the excess ethanol, then removal of the glycerol formed by decantation, the ethyl ester concentration is determined by steric exclusion chromatography. It is 41.2% by mass. This conversion rules out the use of the product obtained as biodiesel fuel.

Example 4

According to the Invention 25 g colza oil, 25 g methanol and 1 g of the catalyst described in example 1 are fed into a 100-ml autoclave reactor equipped with a stirring system and with a temperature and pressure control device. The medium is brought to 200° C. under stirring. The pressure reaches 32 bar (3.2 MPa).

A sample is taken from the liquid phase after a 7-hour reaction. After filtration and evaporation of the excess methanol, then removal of the glycerol formed by decantation, the ester concentration determined by steric exclusion chromatography is 94.9% by mass of esters and 3.4% by mass of monoglycerides, the 100% complement consisting of diglycerides, residual triglycerides, sterols and sterol esters.

At this stage, 20 g of the product obtained above, 20 g ethanol and 1 g of the catalyst described in example 1 are fed into a 100-ml autoclave reactor equipped with a stirring system and with a temperature and pressure control device. The medium is brought to 200° C. under stirring. The pressure reaches 32 bar (3.2 MPa).

A sample is taken from the liquid phase after a 7-hour reaction. After filtration and evaporation of the excess alcohols, then removal of the glycerol formed by decantation, the ester concentration determined by steric exclusion chromatography is 96.9% by mass of esters, 0.7% by mass of monoglycerides, 0.15% by mass of diglycerides and 0.1% by mass of triglycerides, the 100% complement consisting of sterols and of sterol esters. The ethyl ester/methyl ester mass proportion is here 64/36. This composition is compatible with the use thereof as biofuel in a diesel engine.

Thus, the procedure described above allows to prepare a biofuel consisting of fatty acid ethyl esters and fatty acid methyl esters rich in fatty acid ethyl esters, unlike what is obtained in example 3 when the two stages are carried out each in the presence of ethanol.

Example 5

Comparative

This example describes the operating conditions of the method involving two transesterification stages using each a wt. 50/50 methanol/ethanol mixture.

As in example 1, 100 g colza oil and this time 100 g of a wt. 50/50 methanol/ethanol mixture are fed into a fixed-bed reactor containing 110 ml of the same catalyst, at 200° C., at a LHSV of 0.5 h$^{-1}$ (volume of oil per volume of catalyst and per hour), i.e. a reaction time of 55 minutes.

The composition of the reaction mixture at the end of this reaction time is of the order of 92.7% by mass of a mixture of methyl and ethyl esters, the 100% complement consisting of monoglycerides, diglycerides, triglycerides, sterols and sterol esters.

The next stage consists in removing from the reaction medium all of the excess alcohols and in removing, after decantation, the glycerin formed prior to carrying out a second transesterification stage under conditions similar to those of the first stage.

For 100 g of the ester mixture thus obtained, 100 g of the same wt. 50/50 methanol/ethanol mixture is fed at a temperature of 200° C. and at a LHSV of 0.5 h$^{-1}$, which corresponds to a reaction time of 55 minutes.

After total removal of the excess alcohol by distillation and removal of the glycerin formed, the mixture obtained consists of 97.1% by mass of a mixture of fatty acid esters whose ethyl ester/methyl ester mass proportion is 21/79.

With the above procedure where the respective amounts of methanol and ethanol of example 2 throughout the 2 stages were kept, the proportion of ethanol used as biofuel is by far a minority in relation to the methanol, which goes against the result obtained according to the invention in example 2.

The entire disclosure of all applications, patents and publications, cited herein and of corresponding French Application No. 05/09.526, filed Sep. 16, 2005 is incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A method of manufacturing an ester composition comprising ethyl esters of linear monocarboxylic acids having 6 to 26 carbon atoms from a vegetable or an animal oil, neutral or acid, virgin or recycled, said method comprising:
    a stage 1 of transesterifying said vegetable or animal oil with methanol, in the presence of a heterogeneous catalyst comprising a combination of at least one metallic oxide and alumina or a combination of at least two metallic oxides and possibly alumina;
    a stage 2 of transesterifying the resultant methyl ester product from stage 1 with ethanol in the presence of a heterogeneous catalyst as defined in stage 1, so as to produce a mixture rich in said ethyl esters compared to said methyl esters; and wherein prior to stage 2 removing substantially all excess methanol and resultant glycerine from a resultant methyl ester product from stage 1.

2. A method as claimed in claim 1 wherein each one of stages 1 and 2 is carried out at a temperature from 165° C. to 240° C., with a contact time from 15 minutes to 3 hours and an alcohol/feedstock mass ratio from 20/80 to 80/20.

3. A method as claimed in claim 1 wherein the initial oil is selected from among palm oil (concrete or olein), soybean oil, palm nut oil, copra oil, babassu oil, colza oil (old or new), sunflower oil (conventional or oleic), corn oil, cotton oil, tallow and lard, peanut oil, pourgher oil, castor oil, linseed oil and crambe oil, and all the oils obtained from sunflower or colza by genetic engineering or hybridization.

4. A method as claimed in claim 1 wherein the initial oil is selected from waste kitchen oil, slaughterhouse oil, fish oil, seal oil, fowl fat.

5. A method as claimed in claim 1 wherein the initial oil is selected from among oils partly modified by polymerization or oligomerization.

6. A method as claimed in claim 1 wherein the initial oil has an acid number close to 10.

7. A method as claimed in claim 1 wherein the initial oil has an acid number above 10, the transesterification reaction of stage 1 is preceded by an esterification reaction of free fatty acids present with methanol in the presence of a strong acid selected from among sulfuric acid and soluble or supported sulfonic acids.

8. A method as claimed in claim 1 wherein the initial oil having an acid number above 10, the transesterification reaction of stage 1 is preceded by an esterification reaction in the presence of free fatty acids present with glycerin to form a total or partial glycerol ester, in the presence of a heterogeneous catalyst, at atmospheric pressure or under a partial vacuum, and at a temperature ranging between 165° C. and 240° C.

9. A method as claimed in claim 1 wherein said heterogeneous catalyst used in stage 1 or said heterogeneous catalyst used in stage 2 comprises:
    a combination of at least one oxide of at least one metal $M^1$ selected from among the metals of group IIA, group IIB, group IIIA, group IIIB, group IVB, group IVA and group VA with alumina,
    or a combination of at least two oxides of at least one metal $M^1$ and of at least one metal $M^2$ selected from among the metals of group IIA, group IIB, group IIIA, group IIIB, group IVB, group IIIA, group IVA and group VA possibly in the presence of alumina.

10. A method as claimed in claim 9, wherein said heterogeneous catalyst comprises a combination of oxides having the general formula as follows: $(M^1O_x)_y(Al_2O_3)_{(1-y)}$, where x has a value from 1.2 to 2.6 and y representing the mass ratio of the two oxides has a value from 0.005 to 2.

11. A method as claimed in claim 9, wherein said heterogeneous catalyst comprises a combination of oxides having the general formula as follows:

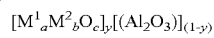

where a has a value from 0.5 to 5, b a value from 0.5 to 5, c is the number of oxygen atoms that satisfies the valence of metals $M^1$ and $M^2$ and y has a value from 0.005 to 1.

12. A method according to claim 1, wherein the resultant mixture rich in ethyl esters has an ethyl ester/methyl ester mass proportion in the range of about 64/36 to about 72/28 and is useable as a biofuel in a diesel engine.

* * * * *